(12) United States Patent
Banko (10) Patent No.: US 10,350,110 B2
(45) Date of Patent: Jul. 16, 2019

(54) DUAL LUMEN SURGICAL WORK TIP FOR PLACING CHEMICALS TO DISSOLVE CATARACTS

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 508 days.

(21) Appl. No.: 14/979,176

(22) Filed: Dec. 22, 2015

(65) Prior Publication Data

US 2016/0106580 A1 Apr. 21, 2016

Related U.S. Application Data

(63) Continuation-in-part of application No. 14/506,404, filed on Oct. 3, 2014, now Pat. No. 10,207,045, which is a continuation-in-part of application No. 14/292,459, filed on May 30, 2014, now Pat. No. 10,179,068, which is a continuation-in-part of
(Continued)

(51) Int. Cl.
| | |
|---|---|
| *A61F 9/00* | (2006.01) |
| *A61F 9/007* | (2006.01) |
| *A61M 1/00* | (2006.01) |
| *A61M 3/02* | (2006.01) |
| *A61F 9/008* | (2006.01) |

(Continued)

(52) U.S. Cl.
CPC ............ *A61F 9/0008* (2013.01); *A61F 9/008* (2013.01); *A61F 9/00736* (2013.01); *A61F 9/00745* (2013.01); *A61M 1/0064* (2013.01); *A61M 3/0283* (2013.01); *A61B 2017/320084* (2013.01); *A61B 2018/263* (2013.01); *A61B 2217/005* (2013.01); *A61B 2217/007* (2013.01); *A61F 2009/0087* (2013.01); *A61F 2009/00887* (2013.01); *A61M 2210/0612* (2013.01)

(58) Field of Classification Search
CPC ................ A61F 9/0008; A61F 9/00745; A61F 2009/0087; A61F 2009/00887; A61F 9/00736; A61F 9/008; A61M 1/0064; A61M 2210/0612; A61M 3/0283; A61B 2217/005; A61B 2217/007; A61B 2017/320084; A61B 2018/263
See application file for complete search history.

(56) References Cited

U.S. PATENT DOCUMENTS

| | | |
|---|---|---|
| 4,425,115 A | 1/1984 | Wuchinich |
| 4,504,264 A | 3/1985 | Kelman |

(Continued)

OTHER PUBLICATIONS

Non Final Office Action dated Feb. 12, 2016 in corresponding U.S. Appl. No. 14/142,555.
(Continued)

*Primary Examiner* — Brandy S Lee
(74) *Attorney, Agent, or Firm* — Leason Ellis LLP (57) ABSTRACT

A method and apparatus for chemically treating a cataract in the eye of a patient comprising the steps of (a) inserting a dual lumen work tip into the eye and placing it adjacent the cataract tissue; (b) causing the work tip to vibrate so that pieces of the cataract separate or emulsify; (c) moving the work tip into the cataract tissue so as to form a tunnel therein; and (d) injecting into the tunnel a pharmaceutical compound capable of treating cataract tissue.

15 Claims, 7 Drawing Sheets

Related U.S. Application Data application No. 14/142,555, filed on Dec. 27, 2013, now Pat. No. 10,166,317, which is a continuation-in-part of application No. 12/215,315, filed on Jun. 26, 2008, now Pat. No. 8,641,658.

(51) Int. Cl.
    *A61B 17/32*      (2006.01)
    *A61B 18/26*      (2006.01)

(56) References Cited

U.S. PATENT DOCUMENTS

| | | |
|---|---|---|
| 4,551,130 A | 11/1985 | Herbert |
| 4,735,604 A | 4/1988 | Watmough |
| 4,750,902 A | 6/1988 | Wuchinich |
| 5,084,013 A | 1/1992 | Takase |
| 5,248,297 A * | 9/1993 | Takase ............... A61M 1/0047 604/22 |
| 5,254,082 A | 10/1993 | Takase |
| 5,817,099 A | 10/1998 | Skolik et al. |
| 6,007,511 A | 12/1999 | Prywes |
| 6,282,442 B1 | 8/2001 | DeStefano et al. |
| 6,309,347 B1 | 10/2001 | Takashi |
| 6,878,142 B2 * | 4/2005 | Lawrence ........... A61M 1/0084 604/28 |
| 7,083,589 B2 | 8/2006 | Banko et al. |
| 7,503,895 B2 | 3/2009 | Rabiner |
| 2002/0022796 A1 | 2/2002 | Lawrence et al. |
| 2002/0161326 A1 | 10/2002 | Sussman et al. |
| 2003/0176791 A1 | 9/2003 | Rabiner et al. |
| 2005/0085769 A1 | 4/2005 | MacMahon |
| 2005/0267400 A1 * | 12/2005 | Haarala ............... A61M 1/3653 604/43 |
| 2006/0173244 A1 | 8/2006 | Boulais et al. |
| 2008/0044790 A1 | 2/2008 | Fani |

OTHER PUBLICATIONS

Non Final Office Action dated Dec. 1, 2016 in corresponding U.S. Appl. No. 14/142,555.
Final Office Action dated Sep. 11, 2017 in corresponding U.S. Appl. No. 14/142,555.
Non Final Office Action dated Jul. 29, 2016 in corresponding U.S. Appl. No. 14/292,459.
Non Final Office Action dated May 18, 2017 in corresponding U.S. Appl. No. 14/292,459.
Non Final Office Action dated Jan. 26, 2018 in corresponding U.S. Appl. No. 14/142,555.
Non Final Office Action dated Feb. 27, 2017 in corresponding U.S. Appl. No. 14/506,404.

* cited by examiner

DUAL LUMEN SURGICAL WORK TIP FOR PLACING CHEMICALS TO DISSOLVE CATARACTS

CROSS-REFERENCE TO RELATED APPLICATIONS

The present application is a continuation-in-part of prior U.S. patent application Ser. No. 14/506,404 filed on Oct. 3, 2014, which is a continuation-in-part of U.S. patent application Ser. No. 14/292,459 filed on May 30, 2014, which is a continuation-in-part of U.S. patent application Ser. No. 14/142,555 filed on Dec. 27, 2013, which in turn is a continuation-in-part of prior U.S. patent application Ser. No. 12/215,315 filed on Jun. 26, 2008 (now U.S. Pat. No. 8,641,658, which issued Feb. 4, 2014). Priority is claimed only to U.S. patent application Ser. No. 14/292,459 filed on May 30, 2014, and U.S. patent application Ser. No. 14/142,555 filed on Dec. 27, 2013, both of which are incorporated herein in their entirety.

TECHNICAL FIELD

The present invention is generally directed to a surgical dual lumen work tip that can be used with an ultrasonic hand piece during surgical procedures including the removal of cataracts from the eye of a patient by phacoemulsification.

BACKGROUND OF THE INVENTION

The use of ultrasonic instruments in surgical applications is well known. One widely used type of instrument is an ultrasonic hand piece that is used in ophthalmic applications, such as in the removal of cataracts from the eye by phacoemulsification.

Recent medical research, i.e., "Ditopic Complexation of Selenite Anions or Calcium Cations by Pirenoxine: An Implication for Anti-Cataractogenesis" (*Inorganic Chemistry*, December 2010: Vol 50, pp 365-377; "Pharmacological chaperone for a -crystallin partially restores transparency in cataract models" (*Science*, November 2015:Vol 350, pp.674-677) and "Lanosterol reverses protein aggregation in cataracts" (*Nature*, Jul. 20, 2015: Vol 523, pp.607-611), which are incorporated herein in their entirety by reference, has demonstrated that treatment by chemical compounds like lanosterol reverses protein aggregation in cataracts. In addition, pharmacological chaperones, e.g., molecules that bind a-crystallins (cryAA and cryAB), used in medical treatment for various diseases are being used to partially restore transparency in cataracts. Eye drops can be one method of delivery for these pharmaceutical compounds. However, it may be advantageous to inject pharmaceutical compounds directly into the tissue that requires treatment.

SUMMARY OF THE INVENTION

In accordance with the invention a dual lumen work tip is provided that can perform all of the functions of emulsification of tissue and other substances by ultrasonic energy, aspiration of such tissue and substances, and also provide a more directed liquid irrigation of a site that is being worked on in order to clean up the site.

The invention provides a novel work tip having a dual separate side-by-side lumen construction, as opposed to the concentric structure of the prior art. The work tip is effectively a unit of two tubes or sections of two tubes. Hereafter the term "tube" refers to a full tube or a section of a tube with each such tube or section having its own lumen. Where sections of tubes are used, at least a portion of such sections are integrated along a common surface. The tubes receive ultrasonic energy from a handpiece that contains piezoelectric or ceramic elements that vibrate at ultrasonic frequencies and contain a connecting body that transmits ultrasonic energy to the dual lumen work tip.

In one mode of operation, phacoemulsification, the dual lumen work tip is inserted into the eye and placed adjacent cataract tissue. The vibration of the tip due to the ultrasonic hand piece causes pieces of the cataract to separate or emulsify. At the same time the site is irrigated, i.e., fluid is inserted into the eye through one of the tubes of the dual lumen work tip, and is withdrawn or aspirated through the other tube of the dual lumen work tip. This has the dual effect of cooling the site where the cataract tissue is being separated and of carrying the pieces of emulsified cataract tissue out the eye with the aspirated fluid.

The aspiration tube can have any desired shape at its working end, in particular any desired shape of its aspiration opening. The irrigation liquid flows through the other tube, i.e., the infusion tube, and its end can have any number of openings or ports in any desired pattern to direct the flow of the irrigation fluid.

The infusion tube is ideal for delivering pharmaceutical compounds to the area that requires treatment. In particular, in a second mode of operation, pharmacological cataract treatment, the ultrasonically vibrating work tip is manipulated in the eye not to emulsify all of the cataract tissue, but to create a tunnel into the center of the tissue where a chamber is formed. This tunneling may be performed with or without the infusion and aspiration of fluid through the lumens of the work tips. For example, if the creation of the tunnel and chamber can be accomplished in a short period of time, the cooling effect of the fluid may not be necessary.

Once the tunnel and chamber have been created and the work tip is deep in the chamber, the infusion tube may be used to inject a chemical compound directly into the chamber of the cataract. This direct application of a pharmacological compound is more effective than delivering the compound in eye drops. Also, the use of the dual lumen to infuse and aspirate the fluid along with the pharmacological compound allows for control of the concentration and duration of the compound in the cataract tissue.

BRIEF DESCRIPTION OF THE DRAWINGS

The foregoing and other objects and advantage of the present invention will become more readily apparent upon reference to the following specification and annexed drawings in which.

DETAILED DESCRIPTION OF THE INVENTION

Figure 1:
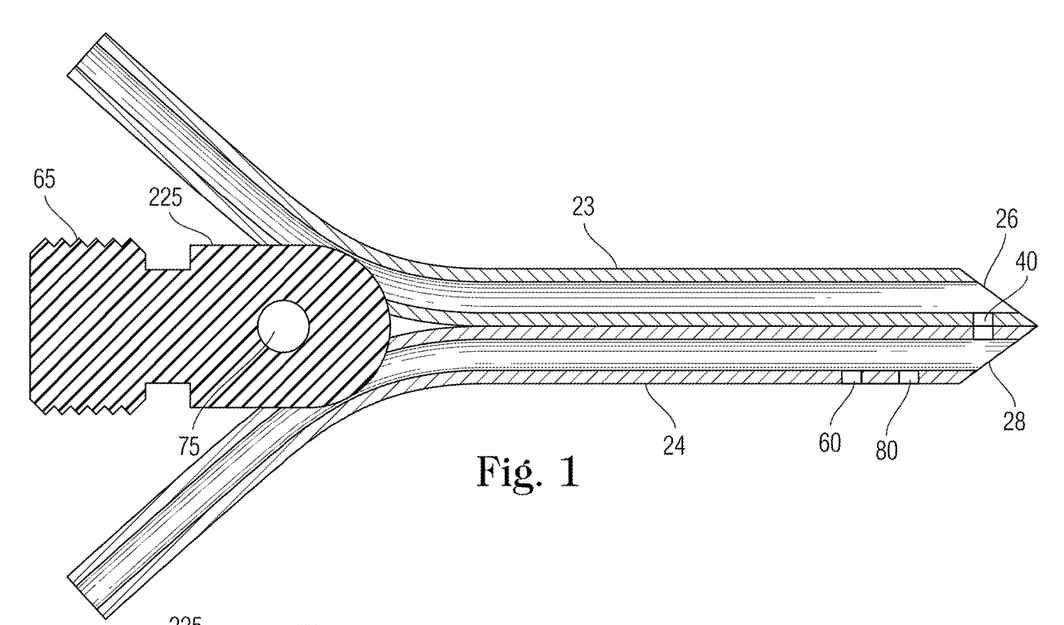
FIG. 1 is a plan view, in cross section of one embodiment of the dual lumen work tip of the present invention.
Figure 4:
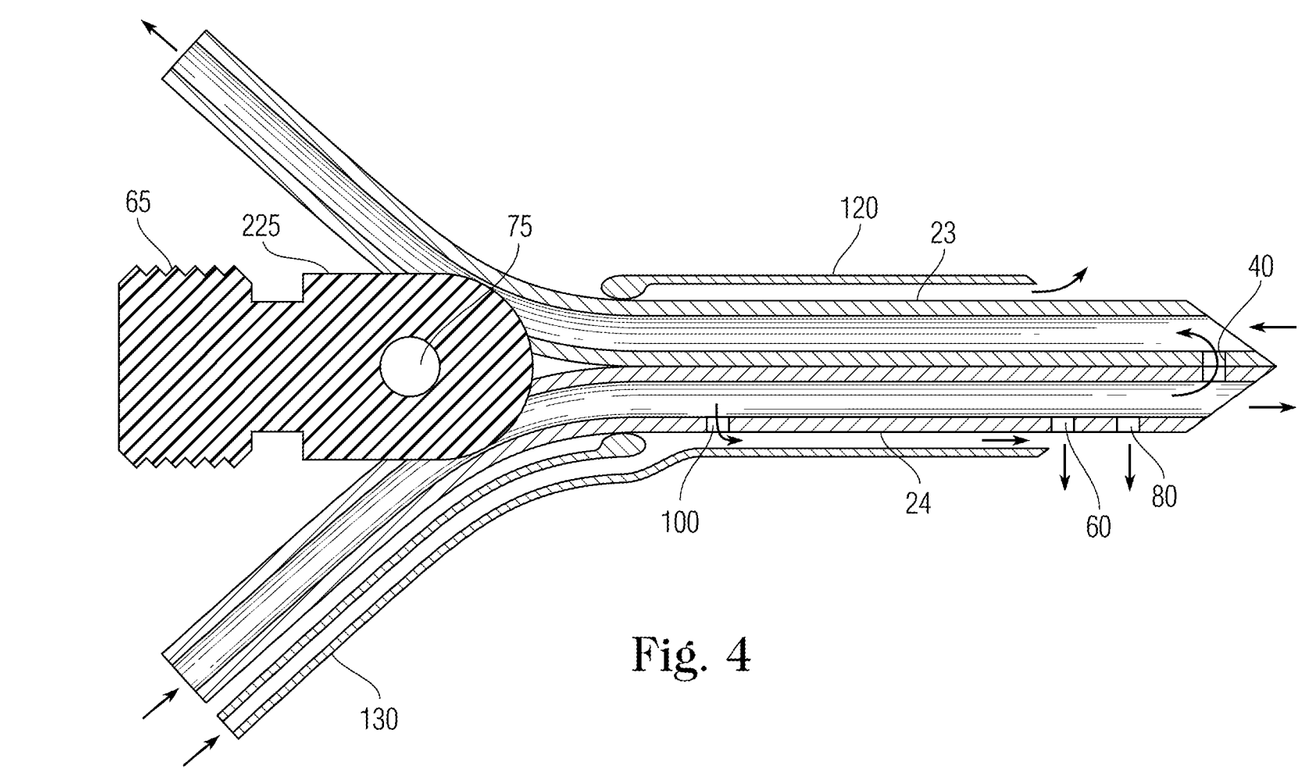
FIG. 4 is a plan view of a second embodiment of the dual lumen work tip with an attached irrigation sleeve.

FIG. 1 shows an embodiment of the work tip of the present invention. Two tubes 23 and 24 are joined together at hub 25 and at various sections where the tubes come in contact with each other. The entire assembly can be connected with thread 65 to an ultrasonic hand piece. Depending on the preference of the surgeon, either one of the two tubes or both of the tubes can irrigate the surgical site or aspirate tissue and fluid from the surgical site. If both tubes aspirate through openings 26 and 28 then a separate infusion source needs to be provided as shown in FIG. 4. The dual lumen tip and hub can be tightened onto the hand piece with a wrench designed to be inserted into opening 75.

The dual lumen work tip shown in FIG. 1 can be used to remove cataracts or any diseased tissue. The work tip can also be used to inject pharmaceutical agents into the lens or any other tissue requiring medication. The advantage of using an ultrasound vibrating dual lumen configuration is that you can gently tunnel into the cataract by using the ultrasonic vibrating tip and form a chamber in which to deposit pharmaceutical agents.

Figure 7:
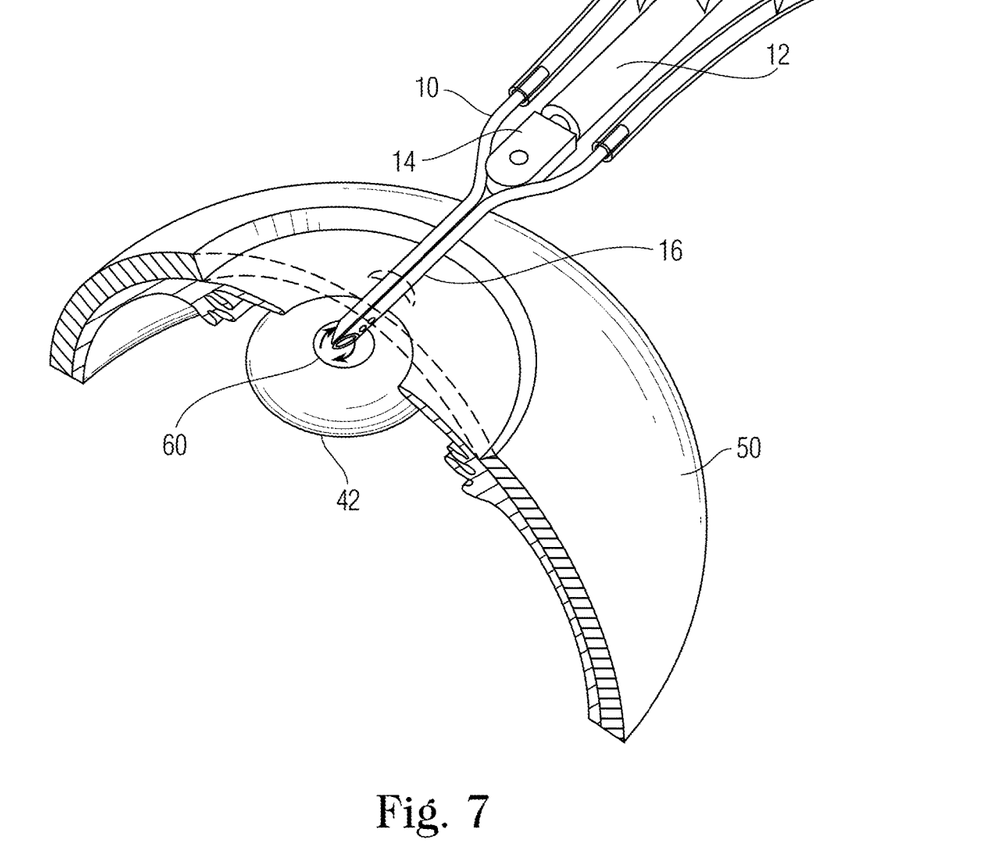
FIG. 7 is a perspective view of the dual lumen work tip used in a medical procedure to treat cataracts.

According to one aspect of the present invention the dual lumen work tip is used to create a chamber in a cataract into which a pharmacological substance is injected to chemically reverse the aggregation of proteins in the cataract. As shown in FIG. 7, a surgical tool 10 has an ultrasonic hand piece 12, a dual lumen hub 14 and a work tip 16. The work tip 16 of the tool 10 is inserted through the cornea of the eye and is placed into the lens 42 of the eye 50 in a manner typical in phacoemulsification procedures. In a typical phacoemulsification procedure the work tip would be vibrated at an ultrasonic frequency by the hand piece. As a result, the tissue of the cataract in the vicinity of the work tip would be emulsified. The site of emulsification would be irrigated by fluid (typically saline solution) through one of the lumens of the work tip and the emulsified cataract tissue and excess saline solution would be aspirated through the other lumen. Essentially the surgeon moves the work tip to engage all of the lens tissue of the lens 42 in order to substantially remove the lens so it can be replaced with an artificial lens. It can be appreciated that this procedure, while successful, imparts significant mechanical trauma to the eye.

Figure 8:
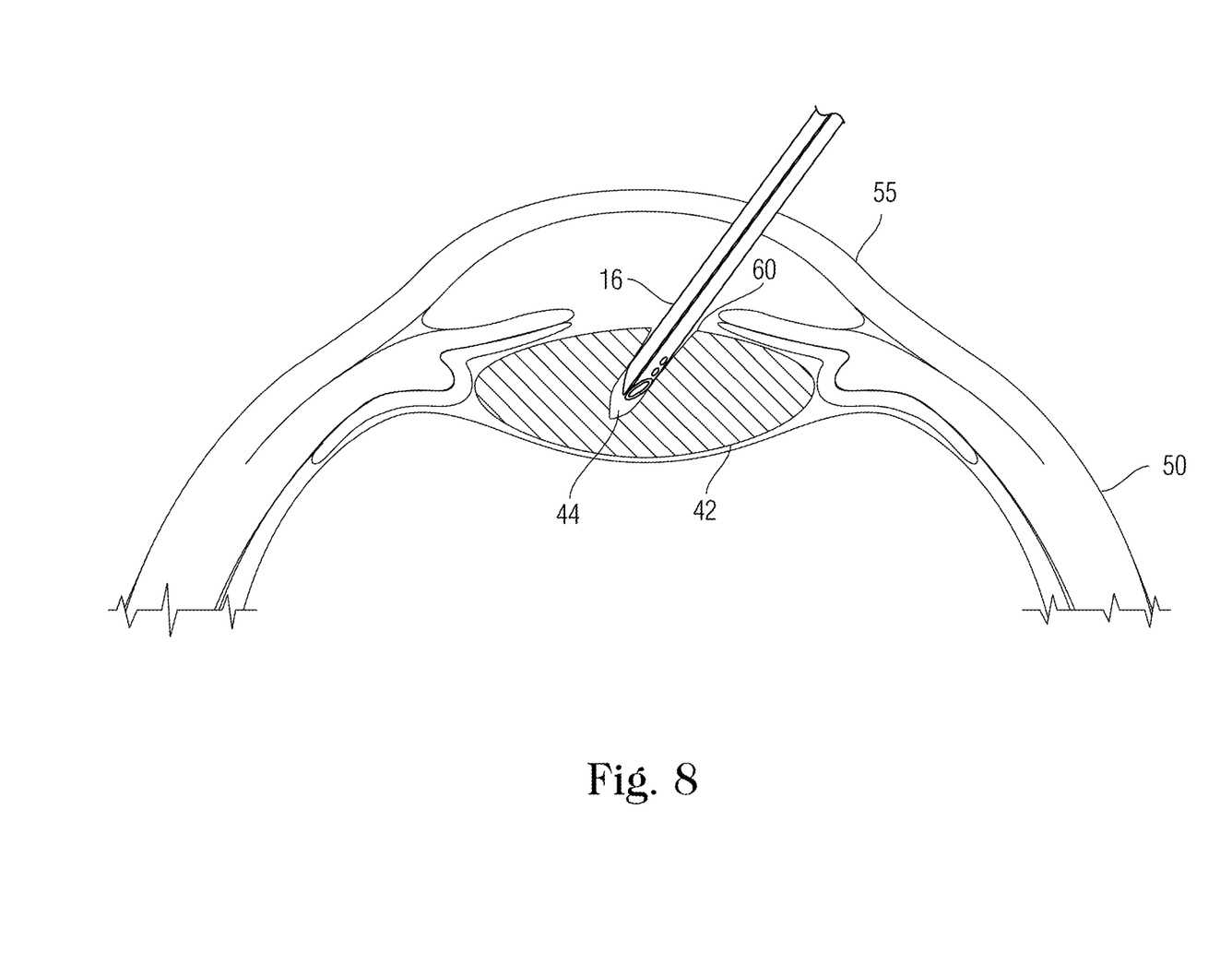
FIG. 8 is a cross sectional view of the procedure of FIG. 7.

According to the present invention, instead of removing all of the lens tissue, the surgeon moves the work tip only to create an opening 60 in the capsular cover of the lens as shown in FIG. 8. It then forms a tunnel 44 in the lens at the location of protein aggregations that are blocking vision. A chamber is located at the bottom of the tunnel 44. Thus, the amount of ultrasonic vibration delivered to the eye is significantly reduced.

During the sculpting of the tunnel in the cataract the aspiration function may be performed with tube 23 through opening 26 and irrigation is provided with tube 24 through opening 28. Irrigation can also be provided through openings 60 and 80. However, if the tunnel and chamber can be made quickly, use of irrigation and aspiration may not be necessary.

After the tunnel is sculpted and the surgeon begins withdrawing the dual tip, the surgeon uses the irrigation lumen to introduce a pharmacological substance into the chamber to chemically reverse the aggregation of the proteins that form the cataract. The effect is to restore at least part of the transparency of the lens. Opening 40 is located between tube 23 and tube 24 near the working tip end. Opening 40 can expedite the removal of tissue through tube 23 by providing a source of additional fluid to help move tissue along tube 23. Also, when penetrating the lens the lumens may be blocked by tissue. Opening 40 allows circulation of the fluid until the blockage is passed.

As indicated in the research literature mentioned above, this substance may be, for example, lanosterol. The prior art introduces these substances into the eye by drops. Thus, the substance came into contact with ocular tissue that did not need it, it was diluted by ocular fluid and it only made contact with the outer surface of the cataract.

The present invention delivers the substance directly to the interior of the cataract and nowhere else. Also, by adjusting the rate of flow of the irrigation and aspiration fluids as well as the timing of their use, the duration and concentration of the substance inside the cataract are significantly controlled.

Figure 2:
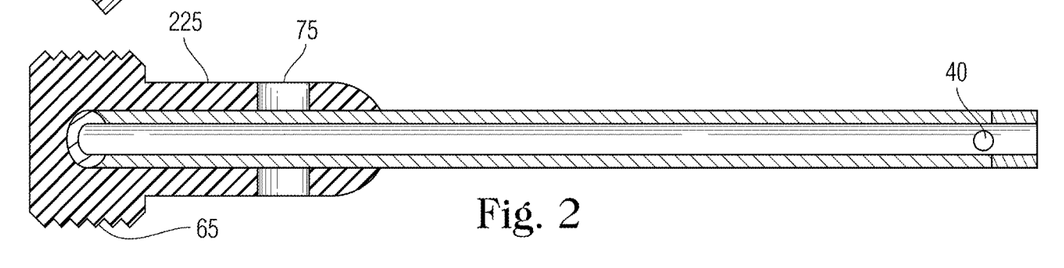
FIG. 2 is an elevation view 90° with respect to the view of FIG. 1 and in cross section of the embodiment of the work tip shown in FIG. 1.

FIG. 2 illustrates a cross section of the dual lumen tip with opening 40 located between tubes 23 and 24.

Figure 3:
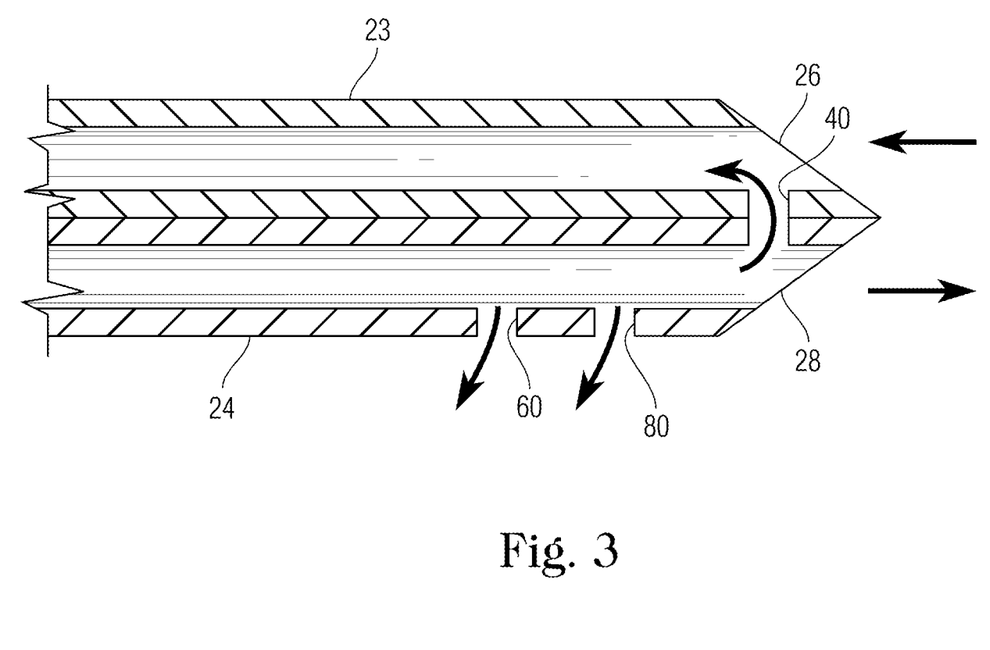
FIG. 3 is an enlarged view of the distal end of the work tip shown in FIG. 1.

FIG. 3 shows a close up of the working tip illustrated in FIG. 1. As the dual lumen tip vibrates tissue may, on occasion, occlude opening 26 and it is advantageous for opening 40 to provide an extra source of fluid to help the removal of tissue from opening 26. Although only one opening is shown at 40 there may be several openings between the tubes 23 and 24.

The dual lumen work tip can provide the aspiration and irrigation function through tubes 23 and 24. However, if the surgeon requires additional irrigation fluid, then a sleeve 120 can be attached to the dual lumen tip which provides another source of irrigation fluid. FIG. 4 illustrates a secondary source of irrigation from tube 130 into sleeve 120. In addition fluid may be provided via tube 24 to sleeve 120 via a hole 100.

Figure 5:
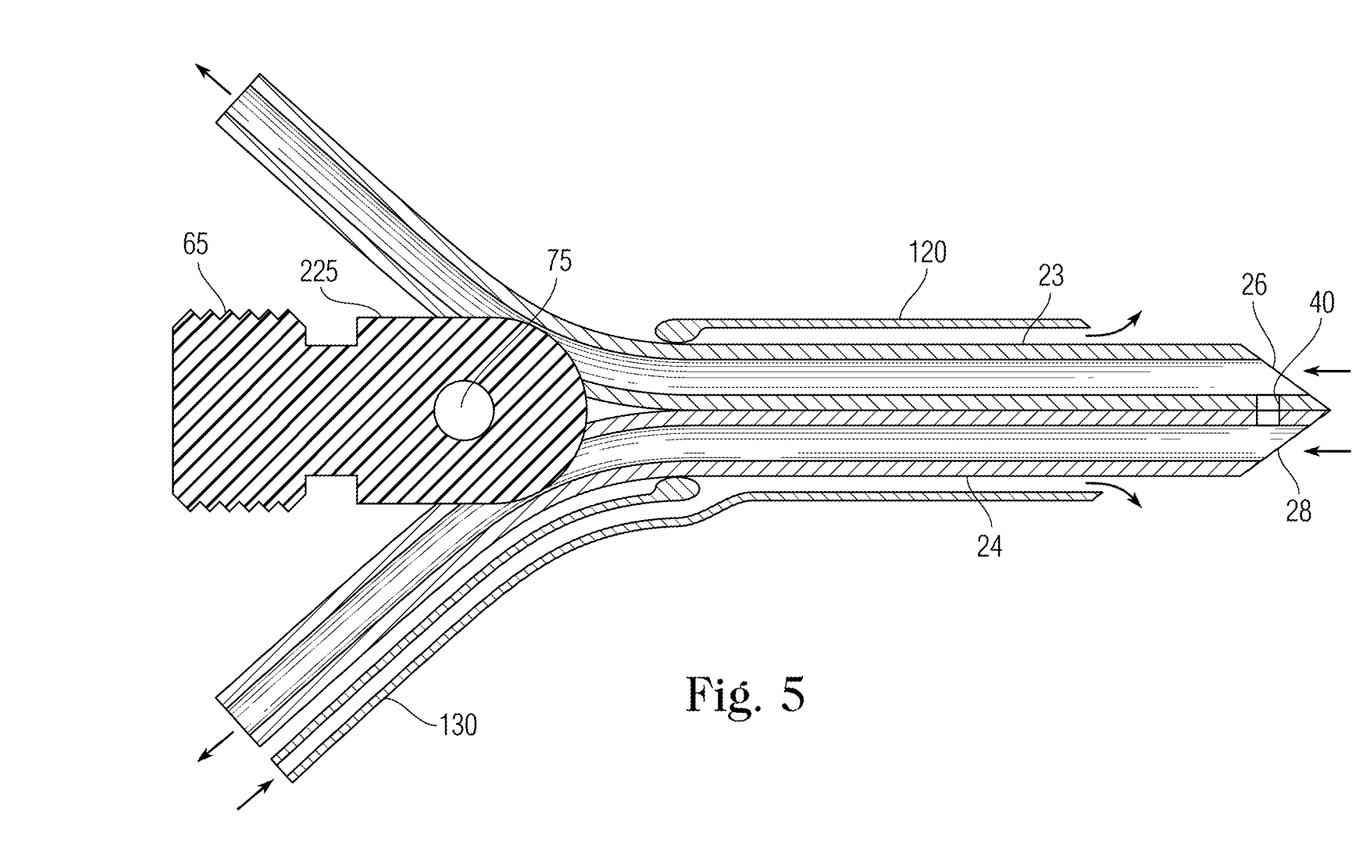
FIG. 5 is a plan view of a third embodiment of the dual lumen work tip wherein an irrigation sleeve is the only source of irrigation.

Another advantage of using a secondary source of irrigation 130 as shown in FIG. 5 is that when the irrigation is sufficient through the external sleeve, then both tubes 23 and 24 can be used to aspirate material through openings 26 and 28. This particular configuration can be used to remove the entire cataract or lens when doing a standard phacoemulsification surgical procedure, as opposed to injecting pharmaceuticals through the dual lumen configuration as shown in FIG. 1.

The dual lumen work tip can be used with or without an ultrasonic hand piece to inject compounds into tissue or to remove sample tissues. The dual lumen work tip can be attached to a non-ultrasonic hand piece, for example a simple handle that the surgeon can hold to direct the dual lumen work tip to the area of the body that requires treatment or tissue removal.

Tissue samples need to be collected for a variety of reasons, for example to make a diagnosis, or tissue can be removed for surgical grafting procedures. The dual lumen work tip can be used to collect tissue samples by having a container to collect the samples attached to the tube that is aspirating the tissue. The second tube can provide either normal saline or any pharmaceutical that may be advantageous during the tissue collection procedure.

Figure 6:
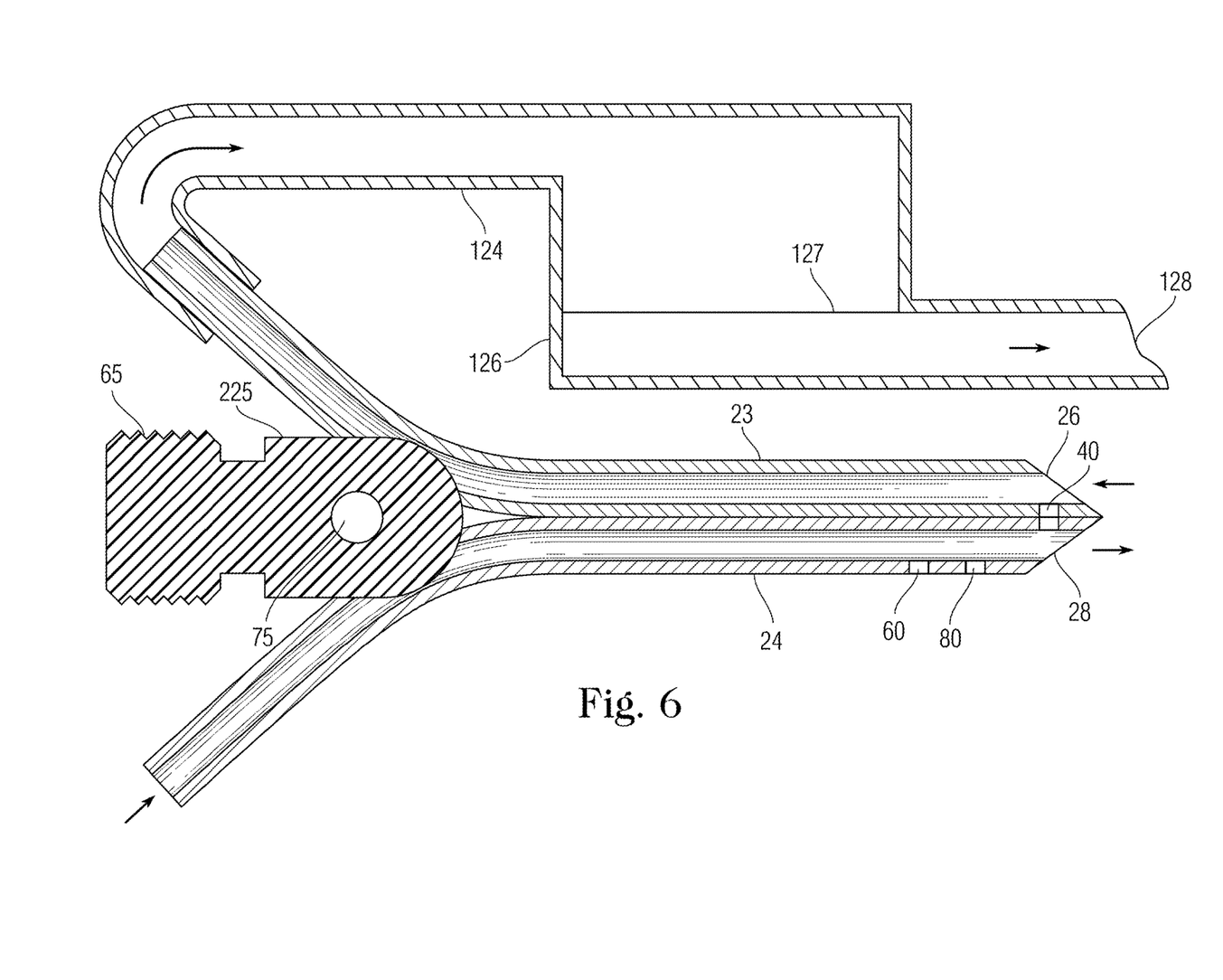
FIG. 6 is a schematic view of the dual lumen work tip of FIG. 1 with a tissue collection container attached to the aspiration tube.

FIG. 6 illustrates a channel 124 attached to tube 23 that is aspirating fluid through opening 26. The fluid and material are collected in a chamber 126, which has a screen 127 at its bottom on which the tissue collects. The fluid with the entrained tissue is moved through tubes 23 and 124 as a result of suction from a pump (not shown) connected to the output 128. Chamber 126, which is removable, is wider than channel 124 so the fluid is slowed before it and the tissue make contact with screen 127.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. A surgical hand piece comprising:
   a handle having a distal end;
   a hub connected to the distal end of the handle;
   a work tip supported by the hub; said work tip having at least first and second tubes supported by the hub but which do not pass through the hub, said at least first and second tubes being aligned side by side and adjacent to each other over a major portion thereof, said at least first and second tubes having proximal external openings connectable to respective first and second fluid sources or drains, each of said at least first and second tubes also having external distal openings;
   wherein each of said at least first and second tubes has a lumen that is adapted to both receive or discharge a fluid at a proximal end of said at least first and second tubes from one of first and second fluid sources or drains that are respectively irrigation and aspiration fluids, the lumen of each of said first and second tubes being separate and spaced apart, and each said at least first and second tubes having an opening at a distal end of said at least first and second tubes through which the fluid is received at or discharged from the proximal end of the respective lumen from each of said at least first and second tubes; and
   wherein the handle is a connecting body, and further including a source of ultrasonic energy attached to the connecting body so as to convey the ultrasonic energy from said ultrasonic energy source to the distal ends of the at least first and second tubes.

2. The surgical hand piece of claim 1 wherein each of said at least first and second tubes has a slanted opening, the slanted opening of a first tube of the at least first and second tubes and the slanted opening of a second tube of the at least first and second tubes being opposite to each other so that combined they from a point.

3. The surgical hand piece of claim 2 further including at least one first opening in the region of the slanted openings connecting the lumens of the at least first and second tubes.

4. The surgical hand piece of claim 1 further including at least one first opening connecting the lumens of the at least first and second tubes.

5. The surgical hand piece of claim 1 further including a sleeve mounted over said at least first and second tubes, said sleeve forming a sleeve channel between an interior surface thereof and an external surface of said at least first and second tubes, said sleeve channel being connectable to a source or drain for fluid.

6. The surgical hand piece of claim 5 wherein both of the at least first and second tubes are connected at their proximal ends to one or two separate sources of fluid so as to provide a dual source of fluid at the distal ends and the sleeve channel is connected to an aspiration source.

7. The surgical hand piece of claim 5 further including at least one passage between the lumen of one of said at least first and second tubes and the sleeve channel.

8. The surgical hand piece of claim 1 wherein both of the at least first and second tubes are connected at their proximal ends to one or two separate sources of fluid so as to provide a dual source of fluid at the distal ends.

9. The surgical hand piece of claim 1 wherein both of the at least first and second tubes are connected at their proximal ends to one or two separate aspiration sources so as to provide dual aspiration of fluid at the distal ends.

10. The surgical hand piece of claim 9 wherein both of the at least first and second tubes are connected at their proximal ends to one or two separate aspiration sources so as to provide dual aspiration of fluid at the distal ends and the sleeve channel is connected to fluid source.

11. The surgical hand piece of claim 1 wherein the first tube is connected at its proximal end to a source of fluid and the second tube is connected at its proximal end to an aspiration source so as to provide fluid circulation at their distal ends.

12. The surgical hand piece of claim 1 wherein passages are formed in at least one of the first or second tube near the distal end.

13. The surgical hand piece of claim 12 further including a sleeve mounted over said at least first and second tubes, said sleeve forming a sleeve channel between an interior surface thereof and an external surface of said at least first and second tubes, said channel being connectable to a source or drain for fluid; and wherein the sleeve ends before the location of the passages near the distal ends of said at least first and second tubes.

14. The surgical hand piece of claim 1 wherein a tube of the least first and second tubes connected to a source of aspiration has a tissue collection container between it and an aspiration source.

15. The surgical hand piece of claim 14 wherein the tissue collection container comprises an enlarged chamber, a screen across the enlarged chamber and an exit channel beyond the screen leading to the aspiration source.

* * * * *